United States Patent [19]

Khokhar et al.

[11] Patent Number: 5,117,022

[45] Date of Patent: *May 26, 1992

[54] HYDROPHOBIC CIS-PLATINUM COMPLEXES EFFICIENTLY INCORPORATED INTO LIPOSOMES

[75] Inventors: Abdul R. Khokhar; Gabriel Lopez-Berestein; Roman Perez-Soler, all of Houston, Tex.

[73] Assignee: The Board of Regents, The University of Texas System, Austin, Tex.

[*] Notice: The portion of the term of this patent subsequent to Aug. 20, 2008 has been disclaimed.

[21] Appl. No.: 234,892

[22] Filed: Aug. 22, 1988

Related U.S. Application Data

[63] Continuation-in-part of Ser. No. 914,591, Oct. 7, 1986, which is a continuation-in-part of Ser. No. 788,850, Oct. 18, 1985, abandoned.

[51] Int. Cl.⁵ .............................................. C07F 15/00
[52] U.S. Cl. .................................... 556/137; 424/450; 514/492
[58] Field of Search .......................................... 556/137

[56] References Cited

U.S. PATENT DOCUMENTS

| | | | |
|---|---|---|---|
| 3,904,663 | 9/1975 | Tobe | 556/137 UX |
| 3,993,754 | 11/1976 | Rahman | 556/137 UX |
| 4,115,418 | 9/1978 | Gale | 556/137 UX |
| 4,137,248 | 1/1979 | Gale | 556/137 UX |
| 4,140,707 | 2/1979 | Cleare | 556/137 UX |
| 4,169,846 | 10/1979 | Kidani | 556/137 UX |
| 4,203,912 | 5/1980 | Hydes | 556/137 UX |
| 4,225,529 | 9/1980 | Hydes | 556/137 UX |
| 4,230,063 | 10/1980 | Hydes | 556/137 UX |
| 4,235,871 | 11/1980 | Papahadjopoulos | 556/137 UX |
| 4,241,046 | 12/1980 | Papahadjopoulos | 556/137 UX |
| 4,256,652 | 3/1981 | Kidani | 556/137 UX |
| 4,271,085 | 6/1981 | Amundsen | 556/137 UX |
| 4,330,534 | 5/1982 | Sakurai | 556/137 UX |
| 4,431,666 | 2/1984 | Bulten | 556/137 UX |
| 4,466,924 | 8/1984 | Verbeek | 556/137 UX |
| 4,522,803 | 6/1985 | Lenk | 556/137 UX |
| 4,657,927 | 4/1987 | Cleare | 556/137 UX |
| 4,661,516 | 4/1987 | Brown | 556/137 UX |
| 4,663,167 | 5/1987 | Lopez-Berestein | 556/137 UX |
| 4,680,308 | 7/1987 | Schwartz | 556/137 UX |
| 4,760,155 | 7/1988 | Heffernan | 556/137 UX |
| 4,760,156 | 7/1988 | Heffernan | 556/137 UX |
| 4,760,157 | 7/1988 | Child | 556/137 UX |

FOREIGN PATENT DOCUMENTS

569425 12/1985 Australia .......................... 556/137

(List continued on next page.)

OTHER PUBLICATIONS

Schwartz et al., Cancer Treatment Reports, 61:1519-1525 (1977).

(List continued on next page.)

Primary Examiner—Paul F. Shaver
Attorney, Agent, or Firm—Arnold, White & Durkee

[57] ABSTRACT

The present invention concerns a platinum (II) four-coordinant complex having the formula:

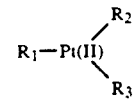

wherein $R_1$ is an alkyl diamine or cycloalkyl diamine and $R_2$ and $R_3$ are an alkylcarboxylato containing from five to ten carbon atoms. The $R_1$ is preferably trans-D,L-1,2-diaminocyclohexane, trans-R,R-1,2-diaminocyclohexane, trans-S,S-1,2-diaminocyclohexane, cis-1,2-diaminocyclohexane ethylene diamine or 1,1-bis(aminomethyl)cyclohexane. The $R_2$ and $R_3$ are preferably neohexanoato, neoheptanoato, neononanoato, neodecanoato, neooctanoato, neopentanoato, 2-ethylhexanoato, 2-ehtylbutyrato, 2-propylpropanoato, 2-methyl-2-ethylheptanoato, 2,2-diethylhexanoato, 2,2-dimethyl-4-ethylhexanoato, 2,2-diethyl-4-methylpentanoato, 2,2-dimethyloctanoato, 2-methyl-2-ethylheptanoato, 2,2-diethylhexanoato, 2,2-diethyl-4-methylpentanoato or 2,2,4,4-tetramethylpentanoato.

In an important further aspect, the present invention involves preparation and therapeutic use of a liposome comprising a phospholipid and a four-coordinate platinum complex having the formula:

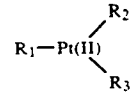

wherein $R_1$ is an alkyl diamine or cycloalkyl diamine and $R_2$ and $R_3$ are an alkylcarboxylato containing from about five to about fourteen carbon atoms. The $R_1$, $R_2$ and $R_3$ functions are preferably as described above with the exception that $R_2$ and $R_3$ may have even longer alkyl chains such as myristate and laurate, i.e., up to fourteen carbon atoms. For therapeutic use, a pharmaceutical composition comprising this liposome and a pharmaceutically acceptable carrier or diluent may be readily prepared by methods well known to those skilled in the art. The liposomes are useful vehicles for solubilizing the otherwise aqueously insoluble complexes of the present invention. The phospholipids of the liposomes may be one or more of phosphatidylglycerol, phosphatidylcholine, sphingomyelin, phosphatidic acid or phosphatidylserine. The liposomes more preferably consist essentially of phosphatidylglycerol, phosphatidylcholine or a combination thereof and may also comprise cholesterol. The liposomes of the present most preferably comprise phospholipid consisting essentially of dimyristoylphosphatidylglycerol, dimyristoylphosphatidylcholine or a combination thereof.

28 Claims, No Drawings

FOREIGN PATENT DOCUMENTS

| | | | |
|---|---|---|---|
| 898614 | 1/1984 | Belgium | 556/137 |
| 113508 | 11/1983 | European Pat. Off. | 556/137 |
| 130482 | 6/1984 | European Pat. Off. | 556/137 |
| 136012 | 8/1984 | European Pat. Off. | 556/137 |
| 193936 | 3/1986 | European Pat. Off. | 556/137 |
| 198765 | 4/1986 | European Pat. Off. | |
| WO86/01102 | 2/1986 | PCT Int'l Appl. | |
| WO87/02364 | 4/1987 | PCT Int'l Appl. | 556/137 |

OTHER PUBLICATIONS

Chemical Abstract 101:177510w, 1984.
Perez-Soler et al., Cancer Research. 47:6462–6466 (Dec. 1987).
Maeda, et al., Japan Journal Cancer Research (Gaann, 77:523–525) (Jun. 1986).
Kihari, Chemical Abstracts 105:134160x.
Craciunescu, Eur, J. Med. Chem. 353–357 (1984).
Sur, Oncology 40:372–376 (1983).
Freise, Archives Internationales de Pharmacodynamie et de Therapie vol. 258–No. 2, Aug. 1982.
Kaledin, Jncl. vol. 66, No. 5, May 1981.
Deliconstantinos, Biochem. Soc. Trans. 5(5):1326–1329 (1977).
Yatvin, Proc. Am. Assoc. Cancer Res. 21:281 (1980).
Szoka, Ann. Rev. Biophys. Bioeng. 9:467–508 (1980).
Schwartz, Chemical Abstracts, 88:16014K (1978).
Perez-Soler, Cancer Research 46, 6269–6273 (1986).
Connors, Chem. Biol. Interactions, 5:415–424 (1972).
Ridgway, J. Clin. Hematol. Oncol. 7:220–229 (1977).
Burchenal, Chemical Abstracts 93:1125661t (1980).
Appleton, Chemical Abstracts 101:182656c (1984).
Speer, Chemical Abstracts 84:54030n (1976).
Khokhar, Chemical Abstracts 103:226308p (1980).
Tzu, Chemical Abstracts 94:218774t (1981).

HYDROPHOBIC CIS-PLATINUM COMPLEXES EFFICIENTLY INCORPORATED INTO LIPOSOMES

This is a continuation-in-part of U.S. patent application Ser. No. 914,591 Oct. 7, 1986, which was a continuation in part of U.S. patent application Ser. No. 788,850, filed Oct. 18, 1985, now abandoned, both of which are incorporated by reference herein.

BACKGROUND OF THE INVENTION

This invention relates to newly synthesized platinum complexes with hydrophobic properties. The use of liposomes incorporating these new and previously synthesized complexes in anti-tumor chemotherapy is also described.

Cis-platinum (CDDP) is a highly effective drug in the treatment of several neoplastic diseases in humans (Loehrer et al. (1984) Ann. Int. Med. V 100, pp 704-713). However, its use is limited by severe systemic toxicity, particularly nephrotoxicity and neurotoxicity (Zwelling et al. Platinum Complexes. In: Pharmacologic principles of cancer treatment (1982) Ed by B. A. Chabner, Saunders, Philadelphia, Pa.). In an attempt to modify the therapeutic index of CDDP, new derivatives have been synthesized during the last decade. However, the sdevelopment of some promising analogues has been prevented by their low hydrosolubility, which decreases their potential for clinical use (Burchenal et al. (1979) Cancer Treat. Rep. V 63, pp 1493-1497).

Liposomes are lipid vesicles which may form spontaneously upon addition of an aqueous solution to a dry lipid film (Mayhew et al., In: Liposomes (1983) Ed by Marc J. Ostro, Marcel Dekker, Inc., New York, N.Y.). Liposomes may be used as drug carriers of hydrophobic or hydrophilic drugs entrapped in their hydrophobic or hydrophilic compartments respectively. Multilamellar liposomes are multilayer lipid vesicles (MLV) that are particularly suited for carrying hydrophobic drugs since their hydrophobic compartment is larger than their hydrophilic compartment. When injected intravenously (iv) in animals, (Kasi et al. (1984) Int. J. Nucl. Med. Biol. V 11 pp 35-37, Lopez-Berestein et al. (1)(1984) Cancer Drug Deliv. V 1, pp 199-205) and humans (Lopez-Berestein et al. (2)(1984), Cancer Res. V 44, pp 375-378), MLV concentrate in the liver, spleen and other organs rich in reticuloendothelial (RES) cells.

Liposomes have been previously used in vitro to deliver chemotherapeutic agents, (Mayhew et al., Liposomes (1983), ed. by Ostro, Marcel Dekker, Inc., New York, N.Y.) and immunomodulators and anti-fungal agents in vitro (Mehta et al. (1984), Immunology V 51 pp 517-527, and in vivo in animals (Lopez-Berestein et al. (4)(1984) Clin Exp Metastasis V 2 pp 127-137 and Lopez-Berestein et al. (1983), J Inf Dis V 147, pp 937-945) and in humans (Lopez-Berestein et al. (1985) J. Inf. Dis. V 151 pp 704-710).

Recent studies show that liposomes can reduce certain types of drug-related toxicities such as doxorubicin cardiotoxicity (Forssen et al. (1981) Proc. Natl. Acad. Sci. V 78 pp 1873-1877, Olson et al. (1982), Eur. J. Cancer Clin. Oncol. V 18 pp 167-176, Gabizon et al. (1982) Cancer Res. V 42 pp 4734-4739, Herman et al. (1983) Cancer Res. V 43 pp 5427-5432) and CDDP nephrotoxicity, (Freise et al. (1982), Arch. Int. Pharmacodynamie Therapie V 258 pp 180-192) and may increase antitumor activity as a result of a slow release mechanism (Mayhew et al. (1978) Ann. N.Y. Acad. Sci. V 308, pp 371-386, Patel et al. (1984) Int. J. Cancer V 34 pp 717-723) a higher drug uptake by tumor cells or due to a more selective organ distribution (Gabizon et al. (1983) Cancer Res. V 43, pp 4730-4735 and Mayhew et al. (1983), Cancer Drug Deliv. V 1 pp 43-58). In U.S. Patent No. 4,330,534 $N^4$-acylcytosine arabinoside incorporated into liposomes, for example, was found to be therapeutically effective when administered to tumor-bearing animals. In spite of these promising results, the clinical application of antitumor agents encapsulated in liposomes has been delayed, mainly due to formulation, drug stability and large scale production problems.

CDDP has been previously encapsulated in MLV but with a very low encapsulation efficiency (7.4%) and poor stability (75% at 48 hours in 0.9% NaCl solution) (Freise et al. (1982) Arch. Int. Pharmacodynamie Therapie V 258 pp 180-192).

In U.S. Pat. No. 4,256,652 are described certain platinum compounds comprising resolved stereoisomers of 1,2 diaminocyclohexane (DACH). The isomers utilized were cis-DACH, trans-RR-1,2-DACH and trans-SS-1,2-DACH. The platinum compounds described therein contained, in addition to a resolved DACH isomer, two hydrophilic platinum ligands such as bromide, iodide, nitrate, bromoacetate, sulfate or glucuronate. The platinum compounds comprising the trans-RR-1,2-DACH were described as often more therapeutically effective than those bearing cis-DACH.

In European Patent Application No. 83306726.7 certain platinum compounds are described which may comprise diaminocyclohexane (non-stereochemically resolved) and do comprise phosphatidyl groups having fatty acid substituents. These compounds are described as largely insoluble in plasma and preferably employed with lipid vesicle carriers The platinum compound-phospholipid vesicles were preferably prepared by a sonic oscillation procedure which characteristically yields unilamellar vesicles.

SUMMARY OF THE INVENTION

The present invention concerns a platinum (II) four-coordinant complex having the formula:

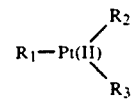

wherein $R_1$ is an alkyl diamine or cycloalkyl diamine and $R_2$ and $R_3$ are an alkylcarboxylato containing from five to ten carbon atoms. The $R_1$ is preferably trans-D,L-1,2-diaminocyclohexane; trans-R,R-1,2-diaminocyclohexane, trans-S,S-1,2-diaminocyclohexane, cis-1,2-diaminocyclohexane ethylene diamine or 1,1-bis(aminomethyl)cyclohexane. The $R_2$ and $R_3$ are preferably neohexanoato, neoheptanoato, neononanoato, neodecanoato, neooctanoato, neopentanoato, 2-ethylhexanoato, 2-ethylbutyrato, 2-propylpropanoato, 2-methyl-2-ethylheptanoato, 2,2-diethylhexanoato, 2,2-dimethyl-4-ethylhexanoato, 2,2-diethyl-4-methylpentanoato, 2,2-dimethyloctanoato, 2-methyl-2-ethylheptanoato, 2,2-diethylhexanoato, 2,2-diethyl-4-methylpentanoato or 2,2,4,4-tetramethylpentanoato.

In an important further aspect, the present invention involves preparation and therapeutic use of a liposome comprising a phospholipid and a four-coordinate platinum complex having the formula:

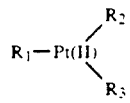

wherein $R_1$ is an alkyl diamine or cycloalkyl diamine and $R_2$ and $R_3$ are an alkylcarboxylato containing from about five to about fourteen carbon atoms. The $R_1$, $R_2$ and $R_3$ functions are preferably as described above with the exception that $R_2$ and $R_3$ may have even longer alkyl chains such as myristate and laurate, i.e., up to fourteen carbon atoms. For therapeutic use, a pharmaceutical composition comprising this liposome and a pharmaceutically acceptable carrier or diluent may be readily prepared by methods well known to those skilled in the art. The liposomes are useful vehicles for solubilizing the otherwise aqueously insoluble complexes of the present invention. The phospholipids of the liposomes may be one or more of phosphatidylglycerol, phosphatidylcholine, sphingomyelin, phosphatidic acid or phosphatidylserine. The liposomes more preferably consist essentially of phosphatidylglycerol, phosphatidylcholine or a combination thereof and may also comprise cholesterol. The liposomes of the present most preferably comprise phospholipid consisting essentially of dimyristoylphosphatidylglycerol, dimyristoylphosphatidylcholine or a combination thereof.

In one preferred aspect, the liposomes of the present invention comprise phospholipid consisting essentially of dimyristoylphosphatidylglycerol and dimyristoylphosphatidylcholine in a ratio between about 1 to 10 and about 10 to 1, more preferably in a ratio of about 3 to 7. These liposomes generally contain the platinum complex and the phospholipid in a ratio between about 1 to 10 and about 1 to 30, more preferably in a ratio of about 1 to 15. The liposomes of of the present invention are preferably multilamellar to enhance encapsulation of the largely hydrophobic platinum complexes.

A significant aspect of the present invention involves a method of treating an animal afflicted with tumor cells sensitive to a platinum (II) four-coordinate complex. This method comprises administering a liposome to the animal, said liposome comprising a phospholipid and a platinum (II) four-coordinant complex having the formula:

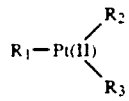

wherein $R_1$ is an alkyl diamine or cycloalkyl diamine and $R_2$ and $R_3$ are an alkylcarboxylato containing from five to fourteen carbon atoms. The various R groups are variable as defined above. The step for administering the lipoosomal platinum (II) complex of the present invention to a tumor-bearing animal is most commonly intravenous injection, intraarterial injection, intramuscular injection, intraperitoneal injection, intrathecal injection, subcutaneous injection, intrapleural injection, topical application or oral dosage. As is the case for most chemotherapy, the administering step is repeated on a timed schedule. To optimize therapeutic effectiveness of the present chemotherapeutic method for inhibiting growth of tumors in a host, a patient bearing a tumor type generally acknowledged to contain cells whose growth is inhibited by platinum (II) complexes should be selected and administering the platinum (II) four coordinate complex of claim 1, 2 or 3 to said host. This platinum (II) four coordinate is most preferably in liposomal form as described above but may be otherwise used if applicable.

DETAILED DESCRIPTION OF PREFERRED EMBODIMENTS

Platinum (II) four-coordinate complexes were prepared utilizing a variety of carboxylato ligands in combination with amino or diamino ligands. Certain of these complexes, either totally new or new as included in liposomes, were, after encapsulation in liposomes, found to be effective in vitro toxins for cancerous cells.

In a general sense, the square-planar platinum (II) four coordinate complexes of the present invention have the formula:

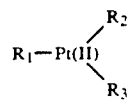

where $R_2$ and $R_3$ are preferably carboxylato monoanions bearing a hydrophobic radical function. Additionally, $R_1$ is preferably a vicinal diaminoalkane or vicinal diaminocycloalkane. It is contemplated that, under some circumstances, $R_1$ may be composed of two independent alkylamines, cycloalkylamines or ammonia although such monoanions have thusfar been less effective. These components confer upon the complex a substantial solubility (normally greater than about 5.0 mg/ml) in methanol or chloroform at ambient temperatures and a substantial insolubility (less than about 0.5 mg/ml) in aqueous solutions at ambient temperatures.

$R_3$ is most preferably trans-SS-1,2-diaminocyclohexane, trans-RR-1,2-diaminocyclohexane, or cis-1,2-diaminocyclohexane.

The hydrophobic radical function, that function covalently pendant from the carboxyl group or from an intermediate or linking group, may be an alkyl, substituted aryl, aryl, alkenyl, cycloalkyl or cycloalkenyl group or even combinations of these functions such as alkylaryl or arylalkenyl, to name but two of the many possible hydrophobic combinations. The hydrophobic radical function characteristically has between 5 and 20 carbon atoms. When this hydrophobic radical function comprises an alkyl or alkenyl group, this group may be straight or branched. Polar functions such as hydroxyl groups, for example, substituted on the hydrophobic radicals would tend to lessen their hydrophobicity and may render them less useful for the purposes of the present invention.

Liposomes containing the platinum (II) complexes described herein may be prepared from various amphipathic substances including natural or synthetic phospholipids. The phospholipids usable to produce liposomes are numerous and not exhaustively listed herein since they are generally well known in the art. These phospholipids include but are not limited to: lecithin, phosphatidylethanolamine, lysolecithin, lysophatidylethanolamine, phosphatidylserine, phosphatidylinositol, sphingomyelin, cardiolipin, phosphatidic acid and the cerebrosides. Most preferable phospholipids for the practice of aspects of the present invention include dimyristoylphosphatidylglycerol (DMPG) and dimyristoylphosphatidylcholine (DMPC). Cholesterol in minor proportions ranging from less than 1% to about 50% may be included with phospholipids and platinum (II) complexes to produce liposomes of the present invention. A preferable but not limiting combination of DMPG and DMPC has been found to be a ratio of 3 to 7 although ratios between 1:10 and 10:1 are contemplated as satisfactory. Ratios of platinum (II) complex to phospholipid between about 1 to 10 and about 1 to 30 are contemplated as generally satisfactory although a 1 to 15 ratio was primarily used in studies thus far.

Either unilamellar or multilamellar or other platinum (II) complex - containing liposomes may be used in the practice of the present invention. Multilamellar liposomes are presently preferred since the platinum (II) complexes of the present invention are substantially water - insoluble and they appear to be incorporated into the phospholipid bilayers of the liposome lamellae.

A procedure for synthesis of the platinum II compounds of the present invention may be generally described. Methods for producing the complexes of the present invention can involve various pathways and intermediates. One pathway involves the utilization of a diiodo (cycloalkyldiamine) platinum (II) complex.

Such diiodo (cycloalkyldiamine) platinum (II) intermediates may be made, for example, by initially combining potassium iodide (e.g., 8 moles, 6.4 molar in water) with potassium tetracloroplatinum (II) (e.g., 1 mole, 0.2 molar in water). This combination results in the formation of 1 mole of potassium tetraiodoplatinum (II).

The tetraiodoplatinum (II) compound is combined with an equimolar amount of cycloalkyldiamine and stirred for about one hour at ambient temperature. A precipitate forms and may be washed with water, ethanol and ether successively, prior to drying. This procedure gives about an 86% yield of diiodo (cycloalkyldiamine) platinum (II).

Example I, shown later herein, specifically shows the preparation of diiodo (trans-R,R-1,2-diaminocyclohexane) platinum (II).

Another intermediate which may be useable for the preparation of the complexes of the present invention is a sulfato (cycloalkyldiamine) platinum (II). For preparation of this compound the diiodo(cycloalkyldiamine) platinum (II) compound described above is mixed with about an equimolar amount of silver sulfate and water. After stirring overnight (protected from light), silver iodide precipitates and may be separated by filtration. The filtrate may then be evaporated to dryness to give a yellow product, i.e. sulfato (cycloalkyldiamine) platinum II complex, in a yield as high as 95% or greater.

For certain routes of platinum complex preparation, a silver carboxylato salt is a preferred intermediate. Such a silver carboxylato salt may be prepared by adding an equimolar amount of silver nitrate (1.25 molar) to a sodium carboxylato salt (0.38 molar) both in water. After stirring at room temperature for about 1 hour (protected from light) the product silver carboxylato salt precipitates in high yield and may be washed with water and dried.

Four exemplary synthetic routes utilizing the above intermediates may be readily described leading to the complexes of the present invention.

Synthetic route #1 involves, for example, the reaction of 1 mole of diiodo(cycloalkyldiamine)platinum (II) with 2 moles of a silver carboxylato salt (0.2 molar in chloroform). After mixing these ingredients, the mixture should be stirred overnight at room temperature and precipitated silver iodide separated by filtration. The filtrate should contain the product cis dicarboxylato (diaminoalkyl) platinum II in high yield.

Synthetic route #2 involves, for example, the reaction of a sulfato(cycloalkyldiamine)platinum II compound (1 mole, 0.08 molar and water with sodium carboxylato salt (4 moles, 0.07 molar in aqueous ethanol 5:1) such a mixture should be stirred for at least about 2 hours and should result in gummy material which may be extracted with chloroform and dried to give the product cis carboxylato(cycloalkyldiamine)platinum (II) complex.

Synthetic route #3 involves, for example, the reaction of sulfato(cycloalkyldiamine)platinum (II) (1 mole, 0.05 molar in water) mixed with a barium carboxylato salt solution prepared by the reaction of barium hydroxide and carboxylato acid in water so that 2 moles of e-carboxylato compound are present. After stirring for three days a precipitate was noted and the final product was extracted in chloraform and dried. The result was the cis carboxylato(cycloalkyldiamine)platinum II complex.

Synthetic route #4 involves the reaction of about 80 mmole potassium iodide with about 10 mmole potassium tetrachloroplatinate (II) in, e.g., 300 ml water are allowed to react to form a dark brown solution and a solution of 1,1-bis(aminomethyl)cyclohexane dihydrochloride and alkali metal hydroxide (20 mmole) in about 30 ml water added dropwise. After stirring at room temperature for about one hour, a precipated product (cis-diiodo[1,1-bis(aminomethyl)cyclohexane platinum (ii) is separated out, for example by filtration, and dried. The product is then reacted with a silver carboxylato salt in a 1:2 molar ratio in chloroform for about 20 hr (protected from light) and precipitated silver iodide separated by filtration. The filtrate is then evaporated to give a light yellow product which may be recrystallized from acetone to give white crystals.

Synthetic routes 1, 2, 3 and 4 are minor synthetic variations and give rise to the same type of platinum complexes while utilizing slightly different chemical routes.

The methods of preparation of particular platinum (II) complexes and chemotherapeutic treatment with particular platinum (II) complexes described in the Examples contained later herein are readily adapted to the production and use of analogously described and claimed complexes by simple substitutions, for example, of appropriate vicinal diamines or hydrophobic radical-containing carboxylato monoanions. The complexes of the present invention which were specifically synthesized and tested are shown in Table 1 with the exception of complexes 4 and 5 all of these complexes are newly synthesized and none have before been included in liposomes.

TABLE 1

| PLATINUM COMPLEXES | |
|---|---|
| Complex # | Complex Name |
| 1. | cis-bis-Neohexanoato (trans-R,R-1,2-DACH*) platinum (II).H$_2$O |
| 2. | cis-bis-Neoheptanoato (trans-R,R-S,S-1,2-DACH) platinum (II) |
| 3. | cis-bis-Neononanoato (trans-R,R-S,S-1,2-DACH) platinum (II) |
| 4. | cis-bis-Laurato (trans-R,R-S,S-1,2-DACH) platinum (II) |
| 5. | cis-bis-Myristato (trans-R,R-S,S-1,2-DACH) platinum (II) |
| 6. | cis-bis-Neohexanoato [1,1-bis |

TABLE 1-continued
PLATINUM COMPLEXES

| Complex # | Complex Name |
|---|---|
| | (aminomethyl)cyclohexane] platinum (II) |
| 7. | cis-bis-Neodecanoato [1,1-bis(aminomethyl)cyclohexane] platinum (II) |
| 8. | cis-bis-Neoheptanoato (trans-R,R-1,2-DACH) platinum (II) |
| 9. | cis-bis-Neoheptanoato [1,1-bis(aminomethyl)cyclohexane] platinum (II) |
| 10. | cis-bis-2,2-dimethyloctanoato (trans-R,R-1,2-DACH) platinum (II) |
| 11. | cis-bis-Neononanoato (trans-R,R-1,2-DACH) platinum (II) |
| 12. | cis-bis-Neoheptanoato (ethylenediamine) platinum (II) |
| 13. | cis-bis-Neopentanoato [1,1-bis(aminomethyl)cyclohexane] platinum (II) |
| 14. | cis-bis-Neononanoato [1,1-bis(aminomethyl)cyclohexane] platinum (II) |
| 15. | cis-bis-2-ethylhexanoato (trans-R,R-S,S-1,2-DACH) platinum (II).H₂O |
| 16. | cis-bis-ethylbutyrato (trans-R,R-S,S-1,2-DACH) platinum (II).H₂O |
| 17. | cis-bis-propylpentanoato (trans-R,R-S,S-1,2-DACH) platinum (II).H₂O |
| 18. | cis-bis-2-methyl-2-ethylheptanoato (trans-R,R-1,2-DACH) platinum (II) |
| 19. | cis-bis-2,2-diethylhexanoato (trans-R,R-1,2-DACH) platinum (II) |
| 20. | cis-bis-2,2-dimethyl-4-ethylhexanoato (trans-R,R-1,2-DACH) platinum (II) |
| 21. | cis-bis-2,2-diethyl-4-methylpentanoato (trans-R,R-1,2-DACH) platinum (II) |
| 22. | cis-bis-2,2-dimethyloctanoato(trans-S,S-1,2-DACH) platinum (II) |
| 23. | cis-bis-2-methyl-2-ethylheptanoato (trans-S,S-1,2-DACH) platinum (II) |
| 24. | cis-bis-2,2-diethylhexanoato (trans-S,S-1,2-DACH) platinum (II) |
| 25. | cis-bis-2,2-diethyl-4-methylpentanoato (trans-S,S-1,2-DACH) platinum (II) |
| 26. | cis-bis-2,2,4,4-tetramethylpentanoato (trans-R,R-1,2-DACH) platinum (II) |
| 27. | cis-bis-neodecanoato (cis-1,2-DACH)Platinum (II) |

*DACH = 1,2 diaminocyclohexane

It is understood that the methods of the present invention include platinum complexes synthesized with analkyl or cycloalkyl diamine and any of numerous alkyl acids with hydrophobic pendant alkyl chains. These alkyl acids include positional isomers of neodecanoic acid not specifically used thusfar. These positional isomers include:

2,2,5-Trimethylheptanoic acid;
2,2,6-Trimethylheptanoic acid;
2,2,4-Trimethylheptanoic acid;
2,2,3-Trimethylheptanoic acid;
2,2,3,5-Tetramethylhexanoic acid;
2,2,4,5-Tetramethylhexanoic acid;
2,2,3,3-Tetramethylhexanoic acid;
2,2,4,4-Tetramethylhexanoic acid;
2,2,5,5-Tetramethylhexanoic acid;

2,2-Dimethyl-3-Ethylhexanoic acid;
2-Ethyl-2,5-Dimethylhexanoic acid;
2-Ethyl-2,4-Dimethylhexanoic acid;

2-Ethyl-2,3-Dimethylhexanoic acid;
2-Ethyl-2,3,4-Trimethylpentanoic acid;
2,3-Diethyl-2-Methylpentanoic acid;

2,2-Diethyl-3-Methylpentanoic acid;
2,2-Diethyl-3,3-Dimethylbutanoic acid;
2,3-Diethyl-2,3-Dimethylbutanoic acid; and 2-Ethyl-2,4,4-Trimethylpentanoic acid.

Liposomes comprising phospholipids and platinum complexes (Pt-liposomes) of the present invention are useful in inhibiting both the growth and metastatic spread of tumors.

Such Pt-liposomes may be administered parenterally, topically or orally. Oral or parenteral dosages of these Pt-liposomes between about 2.5 mg/kg body weight and 25 mg/kg body weight are contemplated as adequate in most conditions. The particular dosages, if a tumor-bearing human is being treated, may vary in each case according to the condition of the patient, the type and extent of tumor, and particular Pt-liposome toxicity.

The amount of liposomal-platinum included in the pharmaceutical composition and the dosage utilized in the method of treatment of the invention will vary depending in each case upon the conditions of the patients, the nature of the tumor undergoing treatment, antitumor activity of liposomal-platinum, the toxicity and solubility characteristics thereof, etc. Liposomal-platinum may also be administered in combination with other antitumor agents in a combined therapeutic regimen.

Parenteral administration may be intraperitoneal, subcutaneous, intrapleural, intrathecal, intraurethral, intravenous, intraarterial, intramuscular or intralymphatic. Such parenteral administration preferably involves Pt-liposome suspensions in pharmaceutically acceptable solutions such as sterile isotonic aqueous solutions. These suspensions may be obtained fully prepared or may be prepared from preformed components. As known to those skilled in the art, Pt-liposomes may be prepared as pellets or powders. These pellets or powders may be mixed with pharmaceutically acceptable solutions to form suspensions for parenteral administration.

Topical administration of Pt-liposomes may involve pharmaceutical compositions such as suspensions, creams or ointments which may be obtained fully prepared or prepared from Pt-liposome powders or pellets. Such topical administration may be near to sites of cancerous lesions such as the epithelium or mucosa for example.

Oral administrations of Pt-liposomes preferably involve encapsulation of Pt-liposome powder or pellets whereby the Pt-liposomes are protected from much gastric and intestinal digestive activity before release from the encapsulation.

When desired, Pt-liposomes may be prepared to contain, for example, other therapeutic agents for treatment of tumors or anti-oxidants to aid in liposome stabilization.

Use of the complexes of the present invention, particularly as a component of liposomes, focuses upon the inhibition of tumor growth and prevention of the metastatic spread of tumors. For example, first a host is identified as bearing a tumor type known to generally contain cells whose growth is often inhibited by platinum (II) complexes. Tumor growth in the host may be inhibited by administering to the host the Pt-containing liposomes of the present invention.

Similarly, the metastatic spread of tumors in a host may be inhibited. A host bearing metastatic or potentially metastatic tumors of a type noted often to be sensitive to platinum (II) complexes, would first be identified. The administration of the Pt-containing liposomes of the present invention to that host would serve to inhibit metastatic spread.

The following examples are presented to further illustrate preferred embodiments of the present invention; they are not intended to limit the invention unless otherwise so stated in the accompanying claims.

EXAMPLE 1

MATERIALS AND ANALYSES

K$_2$PtCl$_4$ was purchased from AESAR (Johnson Matthey, Inc. Seabrook, N.H.). 1,2-diaminocyclohexane (DACH) was purchased from the Aldrich Chemical Co., Milwaukee, Wis. trans-RR-1,2-DACH and trans-SS-1,2-DACH from Morton Thiokol, Inc., Danvers, Mo., cis-1,2-diaminocyclohexane from Turner Labs, Woodland, Tex. and neodecanoic acid from Exxon Chemical Co., Houston, Tex. Elemental analyses of the platinum complexes were performed by Robertson Laboratory, Inc., Madison, N.J. The Liposome Co., Princeton, N.J. synthesized and provided isomerically pure: 2,2-dimethyloctanoic acid; 2,2-dimethyl-4-ethylhexanoic acid; 2-ethyl-2-methylhexanoic acid; 2,2-diethylhexanoic acid; and 2,2-diethyl-4-methylpentanoic acid. Other alkyl acids and reagents were obtained from common commercial sources such as the Exxon Chemical Co.

EXAMPLE 2

THE PREPARATION OF DIIODO (TRANS-R,R-1,2-DIAMINOCYCLOHEXANE) PLATINUM (II)

A solution of potassium iodide (53 g, 0.32 mol.) in 50 ml. of water was added to an aqueous filtered solution of potassium tetrachloroplatinum (II) (16.6 g, 0.04 mol.) in 200 ml. of water. Trans-R,R-1,2-diaminocyclohexane (4.56 g, 0.04 mol.) was added to the potassium tetraiodoplatinum (II) solution. The mixture was kept stirring for one hour at room temperature. The yellow product separated out, which was collected on the filter, washed repeatedly with water, ethanol, either and finally dried under vacuum. Yield (86%).

EXAMPLE 3

THE PREPARATION OF SULFATO (TRANS-R,R-1,2-DIAMINOCYCLOHEXANE) PLATINUM (II)

Diiodo (trans-R,R-1,2-diaminocyclohexane) platinum (II) (16.88 g, 0.03 mol.) was added to a solution of silver sulfate (8.88 g, 0.0285 mol.) in water. The mixture was left stirring overnight at room temperature (protected from light). Silver iodide was separated by filtration and the filtrate was evaporated to dryness under reduced pressure to give a yellow product. The final product was purified from water. Yield (95%).

EXAMPLE 4

THE PREPARATION OF SILVER 2,2-DIMETHYL-4-ETHYLHEXANOATE

A solution of silver nitrate (2.12 g, 12.5 mmol. in 10 ml. of water) was added to a solution of sodium 2,2-dimethyl-4-ethylhexanoate (prepared in situ by mixing 2.5 ml. of 5N NaOH and 2.15 g of 2,2-dimethyl-4-ethylhexanoic acid in 30 ml. of water). A white precipitate formed immediately. The mixture was left stirring at room temperature for one hour (protected from light) which was separated out by filtration, washed repeatedly with water and dried under vacuum. Yield (90%).

EXAMPLE 5

CIS-BIS-NEOHEXANOATO (TRANS-R,R-1,2-DACH) PLATINUM (II). H$_2$O

Complex #1, cis-bis-Neohexanoato (trans-R,R-1,2-DACH) platinum (II). H2O, was synthesized according to synthetic route #2 using neohexanoic acid and trans-R,R-1,2-diaminocyclohexane (DACH). The general structure of cis-bis-Neohexanoato (trans-R,R-1,2-DACH) platinum (II) is as follows:

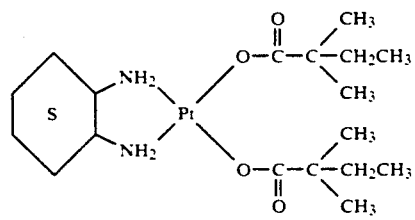

Elemental analysis of cis-bis-Neohexanoato (trans-R,R-1,2-DACH) platinum (II) showed respective percentages for C; H; and N of 38.70%; 6.92%; and 4.91%; as compared to the calculated percentages of 38.78%; 6.82%; and 5.03%.

EXAMPLE 6

CIS-BIS-NEOHEPTANOATO (TRANS-DL-1,2-DACH) PLATINUM (II)

Complex #2, cis-bis-Neoheptanoato (trans-DL-1,2-DACH) platinum (II) was synthesized according to synthetic route #3 using neoheptanoic acid and trans-DL-1,2 diaminocyclohexane (DACH). The general structure of cis-bis-Neoheptanoato (trans-DL-1,2-DACH) platinum (II) is as follows:

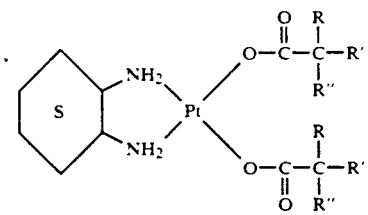

wherein R,R' and R" are each methyl, ethyl, propyl or isopropyl and together have five carbon atoms. Elemental analysis of cis-bis-Neoheptanoato (trans-DL-1,2-DACH) platinum (II) showed respective percentages for C; H; and N of 42.03%; 6.86%; and 4.82%; as compared to the calculated percentages of 42.33%; 7.03%; and 4.94%.

EXAMPLE 7

CIS-BIS-NEONONANOATO (TRANS-DL-1,2-DACH) PLATINUM (II)

Complex #3, cis-bis-Neononanoato (trans-DL-1,2-DACH) platinum (II) was synthesized according to synthetic route #3 using neononanoic acid and trans-DL-1,2-diaminocyclohexane (DACH). The general structure of cis-bis-Neononanoato (trans-DL-1,2-DACH) platinum (II) is as follows:

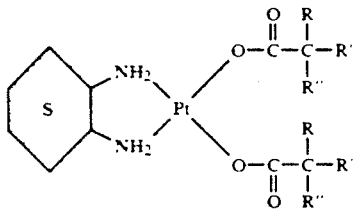

wherein R,R' and R" are each methyl, ethyl, propyl or isopropyl and together have seven carbon atoms. Elemental analysis of cis-bis-Neononanoato (trans-DL-1,2-DACH) platinum (II) showed respective percentages for C; H; and N of 45.99%; 7.69%; and 4.36%; as compared to the calculated percentages of 46.23%; 7.70%; and 4.49%.

EXAMPLE 8

CIS-BIS-LAURATO (TRANS-DL-1,2-DACH) PLATINUM (II)

Complex #4, cis-bis-Laurato (trans-DL-1,2-DACH) platinum (II) was synthesized according to synthetic route #3 using lauric acid and trans-DL-1,2-diaminocyclohexane (DACH). The general structure of cis-bis-Laurato (trans-DL-1,2-DACH) platinum (II) is as follows:

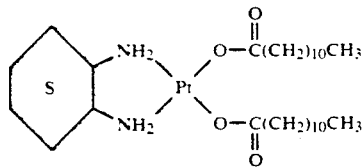

Elemental analysis of cis-bis-Laurato (trans-DL-1,2-DACH) platinum (II) showed respective percentages for C; H; and N of 50.40%; 8.93%; and 3.78%; as compared to the calculated percentages of 50.93%; 8.49%; and 3.96%.

EXAMPLE 9

CIS-BIS-MYRISTATO (TRANS-DL-1,2-DACH) PLATINUM (II)

Complex #5, cis-bis-Myristato (trans-DL-1,2-DACH) platinum (II) was synthesized according to synthetic route #3 using myristic acid and trans-DL-1,2-diaminocyclohexane (DACH). The general structure of cis-bis-Myristato (trans-DL-1,2-DACH) platinum (II) is as follows:

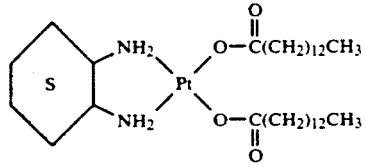

Elemental analysis of cis-bis-Myristato (trans-DL-1,2-DACH) platinum (II) showed respective percentages for C; H; and N of 53.24%; 9.10%; and 3.45%; as compared to the calculated percentages of 53.47%; 8.91%; and 3.67%.

EXAMPLE 10

CIS-BIS-NEOHEXANOATO [1,1-BIS (AMINOMETHYL)CYCLOHEXANE] PLATINUM (II)

Complex #6, cis-bis-Neohexanoato [1,1-bis (aminomethyl)cyclohexane] platinum (II) was synthesized according to synthetic route #4 using neohexanoic acid and 1,1-bis (aminomethyl)cyclohexane. The general structure of cis-bis-Neohexanoato [1,1-bis (aminomethyl)cyclohexane] platinum (II) is as follows:

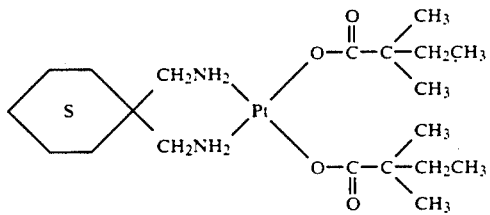

Elemental analysis of cis-bis-Neohexanoato [1,1-bis (aminomethyl)cyclohexane] platinum (II) showed respective percentages for C; H; and N of 42.31%; 7.06%; and 4.90%; as compared to the calculated percentages of 42.33%; 7.05%; and 4.94%.

EXAMPLE 11

CIS-BIS-NEODECANOATO [1,1-BIS (AMINOMETHYL)CYCLOHEXANE] PLATINUM (II)

Complex #7, cis-bis-Neodecanoato [1,1-bis (aminomethyl)cyclohexane] platinum (II) was synthesized according to synthetic route #4 using neodecanoic acid and 1,1-bis (aminomethyl) cyclohexane. The general structure of cis-bis-Neodecanoato [1,1-bis (aminomethyl)cyclohexane] platinum (II) is as follows:

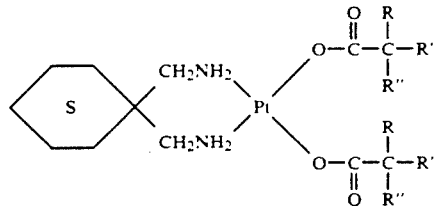

wherein R,R' and R" are each methyl, ethyl, propyl or isopropyl and together have eight carbon atoms.

A solution of potassium iodide (13.3 g, 0.08 mol.) in 30 ml. of potassium tetrachloroplatinate (II) (4.152 g, 10 mmol.) in 300 ml. of water to give a dark brown solution. To this solution a mixture of 1,1-bis(aminomethyl) cyclohexane dihydrochloride (2.15, 10 mmol.) and sodium hydroxide (0.8 g, 20 mmol.) in 30 ml. of water was added dropwise. A light yellow ppt. formed immediately. The mixture was left stirring at room temperature for one hour and the final product was separated out by filtration, washed with 3 x 50 ml. of water and dried under vacuum to give 4.43 g (75%). Cis-diiodo [1,1-bis-(aminomethyl)cyclohexane] platinum (II) (0.9847 g, 1.6 mmol.) was suspended in 150 ml. of CHCl and (0.9296 g, 3.35 mmol.) of silver neodecanoate in 50 ml. of $CHCl_3$ was added dropwise. A clear yellow solution was formed immediately and the reaction mixture was left stirring at room temperature for twenty hours (protected from light). Silver iodide was separated out by filtration and the solvent of the filtrate was evaporated to dryness to give a light yellow product. The final product was recrystallized from acetone to give white crystals. (Yield 79%).

Elemental analysis of cis-bis-Neodecanoato [1,1-bis (aminomethyl)cyclohexane] platinum (II) showed respective percentages for C; H; and N of 49.58%; 8.02%; and 4.09%; as compared to the calculated percentages of 49.48%; 8.25%; and 4.12%.

Other complexes of the invention, i.e. cis-bis-neohexanoato [1,1-bis(aminomethyl)cyclohexane] platinum (II), cis-bis-neoheptanoato [1,1-bis(aminomethyl)cyclohexane] platinum (II), cis-bis-neopentanoato [1,1-bis-(aminomethyl)cyclohexane] platinum (II), and cis-bis-neononanoato [1,1-bis(aminomethyl)cyclohexane] platinum (II) were prepared in an analogous manner to the above mentioned method using stoichiometric amounts of (ca/1 mmole) diiodo[1,1-bis(aminomethyl)cyclohexane] platinum (II), and the respective silver salts of the neo-acids i.e. neohexanoic, neoheptanoic, neopentanoic and neononanoic acid.

EXAMPLE 12

CIS-BIS-NEOHEPTANOATO (TRANS-R,R-1,2-DIAMINOCYCLOHEXANE) PLATINUM (II)

Complex #8, cis-bis-Neoheptanoato (trans-R,R-1,2-DACH) platinum (II) was synthesized according to the procedure of synthetic route #4 using neoheptanoic acid and trans-R,R-1,2-diaminocyclohexane (DACH). The general structure of cis-bis-Neoheptanoato (trans-R,R-1,2-DACH) platinum (II) is as follows:

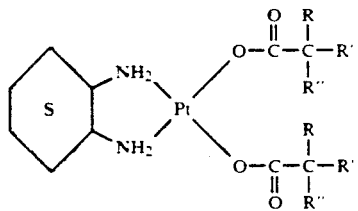

wherein R,R' and R" are each methyl, ethyl, propyl or isopropyl and together have five carbon atoms. Elemental analysis of cis-bis-Neoheptanoato (trans-R,R-1,2-DACH) platinum (II) showed respective percentages for C; H; and N of 41.43%; 6.92%; and 4.84%; as compared to the calculated percentages of 41.66%; 7.12%; and 4.86%.

Sulfato (trans-R,R-1,2-diaminocyclohexane) platinum (II) (0.423 g, 1 mmol.) in 20 ml. of water was mixed with a solution of barium neoheptanoate (prepared in situ by mixing 0.32 g of $Ba(OH)_2 \cdot 8 H_2O$ in 50 ml. of water and 0.26 g of neoheptanoic acid in 20 ml. of ethanol). A white precipitate formed immediately. The mixture was left stirring for three days at room temperature and the final product was extracted in chloroform and was dried over anhydrous magnesium sulfate. The magnesium sulfate was separated by filtration, and the filtrate was evaporated to dryness to give a light yellow product which was purified from acetone. Yield (70%).

Other complexes of the invention, i.e. cis-bis-neoheptanonto (trans-RR,SS-1,2-DACH) platinum (II), cis-bis-neononanoato (trans-RR,SS-1,2-DACH) platinum (II), cis-bis-laurato (trans-RR,SS-1,2-DACH) platinum (II), cis-bis-myristato (trans-RR,SS-1,2-DACH) platinum (II) and cis-bis-2-propylpentanoato (trans-RR,SS-1,2-DACH) platinum (II) were prepared in an analogous manner to the above mentioned method using stoichiometric amounts of (ca/1 mmole) sulfato (trans-RR,SS-1,2-DACH) platinum and the respective barium salts of neoheptanoic, neohexanoic, lauric, myristic and 2-propylpentanoic acid.

EXAMPLE 13

CIS-BIS-NEOHEPTANOATO [1,1-BIS (AMINOMETHYL)CYCLOHEXANE] PLATINUM (II)

Complex #9, cis-bis-Neoheptanoato [1,1-bis (aminomethyl)cyclohexane] platinum (II) was synthesized according to synthetic route #4 using neoheptanoic acid and 1,1-bis (aminomethyl)cyclohexane. The general structure of cis-bis-Neoheptanoato [1,1-bis (aminomethyl)cyclohexane] platinum (II) is as follows:

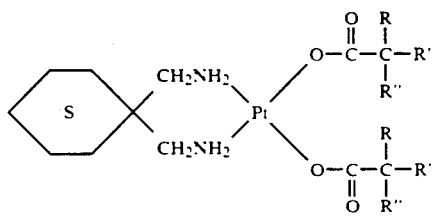

wherein R,R' and R" are each methyl, ethyl, propyl or isopropyl and together have five carbon atoms. Elemental analysis of cis-bis-Neoheptanoato [1,1-bis (aminomethyl)cyclohexane]platinum (II) showed respective percentages for C; H; and N of 43.98%; 7.91%; and 4.18%; as compared to the calculated percentages of 44.37%; 7.39%; and 4.70%.

EXAMPLE 14

CIS-BIS-2,2-DIMETHYLOCTANOATO (TRANS-R,R-1,2-DACH) PLATINUM (II)

Complex #10, cis-bis-2,2-dimethyloctanoato (trans-R,R-1,2-DACH) platinum (II) was synthesized according to synthetic route #2 using bis-2,2-dimethyloctanoic acid and trans-R,R-1,2-diaminocyclohexane (DACH). The general structure of cis-bis-2,2-dimethyloctanoato (trans-R,R-1,2-DACH) platinum (II) is as follows:

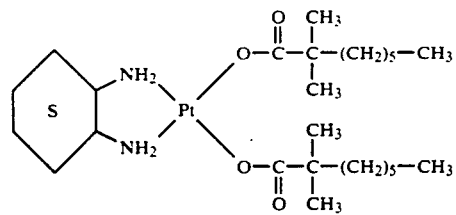

Elemental analysis of cis-bis-2,2-dimethyloctanoato (trans-R,R-1,2-DACH) platinum (II) showed respective percentages for C; H; and N of 47.22%; 7.26%; and 3.94%; as compared to the calculated percentages of 47.92%; 7.99%; and 4.30%.

Sulfato (trans-R,R-1,2-diaminocyclohexane) platinum (II) (0.84 g, 2 mmol.) in 25 ml. of water was added to a solution of sodium 2,2-dimethyloctanoate (prepared in situ by mixing 0.8 ml. of 5N NaOH and 0.688 g (4 mmol.) of 2,2-dimethyloctanoic acid in 10 ml. of ethanol and 50 ml. of water). The mixture was left stirring for two hours and the resulting gummy material was extracted in chloroform and was dried over anhydrous magnesium sulfate. The magnesium sulfate was separated by filtration and the filtrate was evaporated to dryness to give a light yellow product which was purified from acetone. Yield (77%).

EXAMPLE 15

CIS-BIS-NEONONANOATO (TRANS-R,R-1,2-DACH) PLATINUM (II)

Complex #11, cis-bis-Neononanoato (trans-R,R-1,2-DACH) platinum (II) was synthesized according to synthetic route #1 using neononanoic acid and trans-R,R-1,2-diaminocyclohexane (DACH). The general structure of cis-bis-Neononanoato (trans-R,R-1,2-DACH) platinum (II) is as follows:

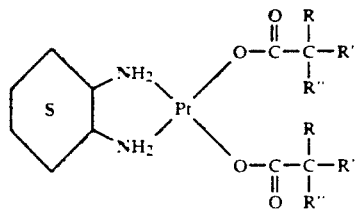

wherein R,R' and R" are each methyl, ethyl, propyl or isopropyl and together have seven carbon atoms. Elemental analysis of cis-bis-Neononanoato (trans-R,R-1,1-DACH) platinum (II) showed respective percentages for C; H; and N of 45.40%; 8.48%; and 4.5%; as compared to the calculated percentages of 46.22%; 4.70%; and 4.49%.

EXAMPLE 16

CIS-BIS-NEOHEPTANOATO (ETHYLENEDIAMINE) PLATINUM (II)

Complex #12, cis-bis-Neoheptanoato (ethylenediamine) platinum (II) was synthesized according to synthetic route #1 using neoheptanoic acid and ethylenediamine. The general structure of cis-bis-Neoheptanoato (ethylenediamine) platinum (II) is as follows:

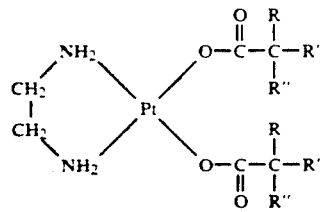

wherein R,R' and R" are each methyl, ethyl, propyl or isopropyl and together have five carbon atoms. Elemental analysis of cis-bis-Neoheptanoato (ethylenediamine) platinum (II) showed respective percentages for C; H; and N of 39.96%; 6.67%; and 5.24%; as compared to the calculated percentages of 37.43%; 6.33%; and 5.46%.

EXAMPLE 17

CIS-BIS-NEOPENTANOATO [1,1-BIS (AMINOMETHYL)CYCLOHEXANE] PLATINUM (II)

Complex #13, cis-bis-Neopentanoato [1,1-bis (aminomethyl)cyclohexane] platinum (II) was synthesized according to synthetic route #4 using neopentanoic acid and 1,1-bis (aminomethyl)cyclohexane. The general structure of cis-bis-Neopentanoato [1,1-bis (aminomethyl)cyclohexane] platinum (II) is as follows:

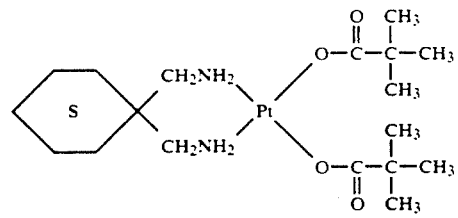

Elemental analysis of cis-bis-Neopentanoato [1,1-bis (aminomethyl)cyclohexane] platinum (II) showed respective percentages for C; H; and N of 38.59%; 6.04%; and 4.54%; as compared to the calculated percentages of 40.07%; 6.68%; and 5.19%.

EXAMPLE 18

CIS-BIS-NEONONANOATO [1,1-BIS (AMINOMETHYL)CYCLOHEXANE] PLATINUM (II)

Complex #14, cis-bis-Neononanoato [1,1-bis (aminomethyl)cyclohexane] platinum (II) was synthesized according to synthetic route #4 using neononanoic acid and 1,1-bis (aminomethyl)cyclohexane. The general structure of cis-bis-Neononanoato [1,1-bis (aminomethyl)cyclohexane] platinum (II) is as follows:

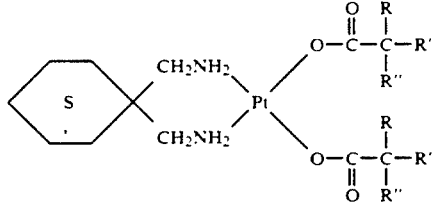

wherein R,R' and R" are each methyl, ethyl, propyl or isopropyl and together have seven carbon atoms. Elemental analysis of cis-bis-Neononanoato [1,1-bis (aminomethyl)cyclohexane] platinum (II) showed respective percentages for C; H; and N of 47.43%; 7.14%; and 3.90%; as compared to the calculated percentages of 47.92%; 7.99%; and 4.30%.

EXAMPLE 19

CIS-BIS-2-ETHYLHEXANOATO (TRANS-DL-1,2-DACH) PLATINUM (II) . H$_2$O

Complex #15, cis-bis-2-ethylhexanoato (trans-DL-1,2-DACH) platinum (II) H$_2$O was synthesized according to synthetic route #2 using 2-ethyl hexanoic acid and trans-DL-1,2-diaminocyclohexane (DACH). The general structure of cis-bis-2-ethylhexanoato (trans-DL-1,2-DACH) platinum (II) is as follows:

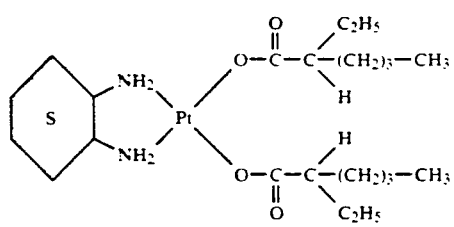

Elemental analysis of cis-bis-2-ethylhexanoato (trans-DL-1,2-DACH) platinum (II) showed respective percentages for C; H; and N of 43.29%; 7.74%; and 4.31%; as compared to the calculated percentages of 43.21%; 7.53%; and 4.58%.

EXAMPLE 20

CIS-BIS-2-ETHYLBUTYRATO (TRANS-DL-1,2-DACH) PLATINUM (II) . $H_2O$

Complex #16, cis-bis-2-ethylbutyrato (trans-DL-1,2-DACH) platinum (II) $H_2O$ was synthesized according to synthetic route #2 using 2-ethylbutyric acid and trans-DL-diaminocyclohexane (DACH). The general structure of cis-bis-2-ethylbutyrato (trans-DL-1,2-DACH) platinum (II) is as follows:

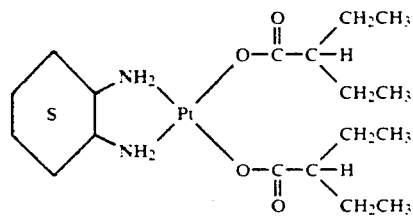

Elemental analysis of cis-bis-2-ethylbutyrato (trans-DL-1,2-DACH) platinum (II) showed respective percentages for C; H; and N of 38.28%; 6.56%; and 4.71%; as compared to the calculated percentages of 38.78%; 6.82%; and 5.03%.

EXAMPLE 21

CIS-BIS-2-PROPYLPENTANOATO (TRANS-DL-1,2-DACH) PLATINUM (II) .$H_2O$

Complex #17, cis-bis-propylpentanoato (trans-DL-1,2-DACH) platinum (II). H 0 was synthesized according to synthetic route #3 using 2-propylpentanoic acid and trans-DL-1,2-diaminocyclohexane (DACH). The general structure of cis-bis-2-propylpentanoato (trans-DL-1,2-DACH) platinum (II) is as follows:

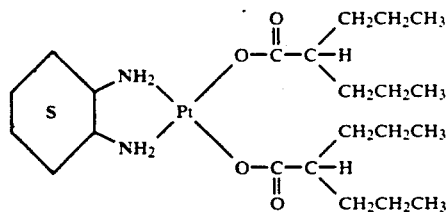

Elemental analysis of cis-bis-2-propylpentanoato (trans-b 1,2-DACH) platinum (II) showed respective percentages for C; H; and N of 43.11%; 7.10%; and 4.59%; as compared to the calculated percentages of 43.71%; 7.45%; and 4.64%.

EXAMPLE 22

CIS-BIS-2-METHYL-2-ETHYLHEPTANOATO (TRANS-R,R-1,2-DACH) PLATINUM (II)

Complex #18, cis-bis-2-methyl-2-ethylheptanoato (trans-R,R-1,2-DACH) platinum (II) was synthesized according to synthetic route #2 using 2-methyl-2-ehtylheptanoic acid and diaminocyclohexane (DACH). The general structure of cis-bis-2-methyl-2-ethylheptanoato (trans-R,R-1,2-DACH) platinum (II) is as follows:

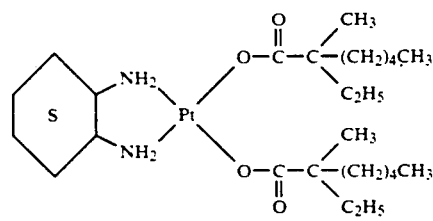

Elemental analysis of cis-bis-2-methyl-2-ethylheptanoato (trans-R,R-1,2-DACH) platinum (II) showed respective percentages for C; H; and N of 43.75%; 7.69%; and 4.23%; as compared to the calculated percentages of 47.92%; 7.99%; and 4.30%.

EXAMPLE 23

CIS-BIS-2,2-DIETHYLHEXANOATO (TRANS-R,R-1,2-DACH) PLATINUM (II)

Complex #19, cis-bis-2,2-diethylhexanoato (trans-R,R-1,2-DACH) platinum (II) was synthesized according to synthetic route #2 using 2,2-diethylhexanoic acid and trans-R,R-1,2-diaminocyclohexane (DACH). The general structure of cis-bis-2,2-diethylhexanoato (trans-R,R-1,2-DACH) platinum (II) is as follows:

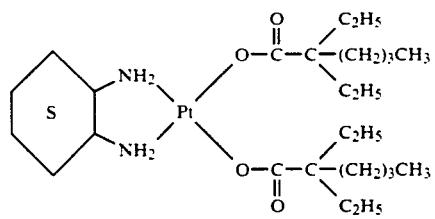

Elemental analysis of cis-bis-2,2-diethylhexanoato (trans-R,R-1,2-DACH) platinum (II) showed respective percentages for C; H; and N of 47.08%; 7.38%; and 4.05%; as compared to the calculated percentages of 47.92%; 7.99%; and 4.30%.

EXAMPLE 24

CIS-BIS-2,2-DIMETHYL-4-ETHYLHEXANOATO (TRANS-R,R-1,2-DACH) PLATINUM (II)

Complex #20, cis-bis-2,2-dimethyl-4-ethylhexanoato (trans-R,R-1,2-DACH) platinum (II) was synthesized according to synthetic route #2 using 2,2-dimethyl-4-ethylhexanoic acid and trans-R,R-1,2-diaminocyclohexane (DACH). The general structure of cis-bis-2,2-dimethyl-4-ethylhexanoato (trans-R,R-1,2-DACH) platinum (II) is as follows:

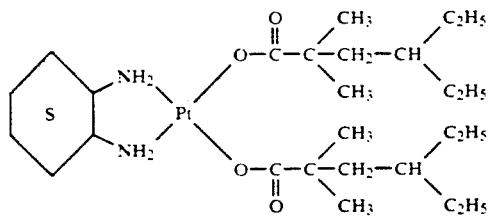

Diiodo (trans-R,R-1,2-diaminocyclohexane) platinum (II) (0.84 g, 1.5 mmol.) was added as a solid to a solution of silver 2,2-dimethyl-4-ethylhexanoate (0.83 g, 3 mmol.) in 150 ml of chloroform. The mixture was kept on stirring overnight at room temperature (protected from light). Silver iodide was separated by filtration and the filtrate was evaporated to dryness to give a light yellow product which was purified from acetone to give a white product. Yield (73%).

Elemental analysis of cis-bis-2,2-dimethyl-4-ethylhexanoato (trans-R,R-1,2-DACH) platinum (II) showed respective percentages for C; H; and N of 47.63%; 7.70%; and 4.08%; as compared to the calculated percentages of 47.92%; 7.99%; and 4.30%.

Other complexes of the invention, i.e. cis-bis-neoheptanoato (trans-R,R-1,2-DACH) platinum (II), cis-bis-neononanoato (trans-R,R-1,2-DACH) platinum (II), cis-bis-2,2,4,4-tetramethylpentanoato (trans-R,R-1,2-DACH) platinum (II) and cis-bis-neoheptanoato (ethylenediamine) platinum (II) were prepared in an analogous manner to the above mentioned method using stoichiometric amounts of appropriate diamine diiodoplatinum (II), and silver salt of respective neo acid.

EXAMPLE 25

CIS-BIS-2,2-DIETHYL-4-METHYLPENTANOATO (TRANS-R,R-1,2-DACH) PLATINUM (II)

Complex #21, cis-bis-2,2-diethyl-4-methylpentanoato (trans-R,R-1,2-DACH) platinum (II) was synthesized according to synthetic route #2 using 2,2-diethyl-4-methylpentanoic acid and trans-R,R-1,2-diaminocyclohexane (DACH). The general structure of cis-bis-2,2-diethyl-4-methylpentanoato (trans-R,R-1,2-DACH) platinum (II) is as follows:

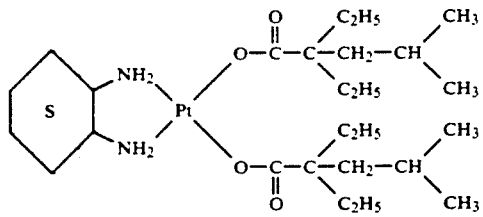

Elemental analysis of cis-bis-2,2-diethyl-4-methylpentanoato (trans-R,R-1,2-DACH) platinum (II) showed respective percentages for C; H; and N of 47.64%; 7.75%; and 4.16%; as compared to the calculated percentages of 47.92%; 7.99%; and 4.30%.

EXAMPLE 26

CIS-BIS-2,2-DIMETHYLOCTANOATO (S,S-1,2-DIAMINOCYCLOHEXANE) PLATINUM (II)

Complex #22, cis-bis-2,2-dimethyloctanoato (trans-S,S-1,2-DACH) platinum (II) was synthesized according to synthetic route #2 using 2,2-dimethyloctanoic acid and trans-S,S-1,2-diaminocyclohexane (DACH). The general structure of cis-bis-2,2-dimethyloctanoato (trans-S,S-1,2-DACH) platinum (II) is as follows:

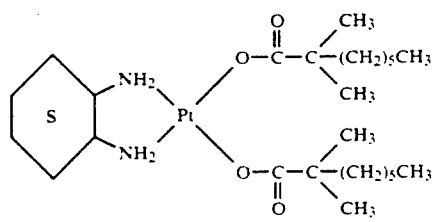

Elemental analysis of cis-bis-2,2-dimethyloctanoato (trans-S,S-1,2-DACH) platinum (II) showed respective percentages for C; H; and N of 47.63%; 8.05%; and 4.15%; as compared to the calculated percentages of 47.92%; 7.99%; and 4.30%.

In summary, complexes of the invention synthesized by this general procedure include, i.e. cis-bis-neoneptanoato (trans-R,R-1,2-DACH) platinum (II), cis-bis-dimethyloctanoato (trans-R,R-1,2-DACH) platinum (II), cis-bis-2-ethylhexanoato (trans,RR,SS-1,2-DACH) platinum (II), cis-bis-2-ethylbutyrato (trans-R,R-1,2-DACH) platinum (II), cis-bis-2-metyl-2-ethylheptanoato (trans-R,R-1,2-DACH) platinum (II), cis-bis-2,2-diethylhexanoato (trans-R,R-1,2-DACH) platinum (II), cis-bis-2,2-dimethyl-4-ethylhexanoato (trans-R,R-1,2-DACH) platinum (II), cis-bis-2,2-diethyl-4-methylpentanoato (trans-R,R-1,2-DACH) platinum (II), cis-bis-2,2-dimethyloctanoato (trans-S,S-1,2-DACH) platinum (II), cis-bis-2-methyl-2-ethylheptanoato (trans-S,S-1,2-DACH) platinum (II), and cis-bis-2,2-diethylhexanoato (trans-S,S-1,2-DACH) platinum (II) were prepared in an analogous manner to the above mentioned method using stoichiometric amounts (ca/mmole) of appropriate sulfato (DACH) platinum (II) and sodium salt of appropriate neo-acid.

EXAMPLE 27

CIS-BIS-2-METHYL-2-ETHYLHEPTANOATO (TRANS-S,S-1,2-DACH) PLATINUM (II)

Complex #23, cis-bis-2-methyl-2-ethylheptanoato (trans-S,S-1,2-DACH) platinum (II) was synthesized according to synthetic route #2 using 2-methyl-2-ethylheptanoic acid and trans-S,S-1,2-diaminocyclohexane (DACH). The general structure of cis-bis-2-methyl-2-ethylheptanoato (trans-S,S-1,2-DACH) platinum (II) is as follows:

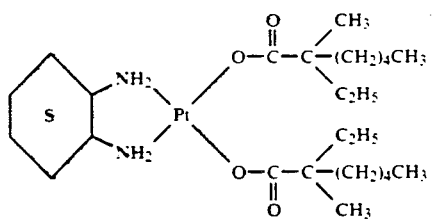

Elemental analysis of cis-bis-2-methyl-2-ethylheptanoato (trans-S,S-1,2-DACH) platinum (II) showed respective percentages for C; H; and N of 47.77%; 8.01%; and 4.15%; as compared to the calculated percentages of 47.92%; 7.99%; and 4.30%.

EXAMPLE 28

CIS-BIS-2,2-DIETHYLHEXANOATO (TRANS-S,S-1,2-DACH) PLATINUM (II)

Complex #24, cis-bis-2,2-diethylhexanoato (trans-S,S-1,2-DACH) platinum (II) was synthesized according to synthetic route #2 using 2,2-diethylhexanoic acid and trans-S,S-1,2-diaminocyclohexane (DACH). The general structure of cis-bis-2,2-diethylhexanoato (trans-S,S-1,2-DACH) platinum (II) is as follows:

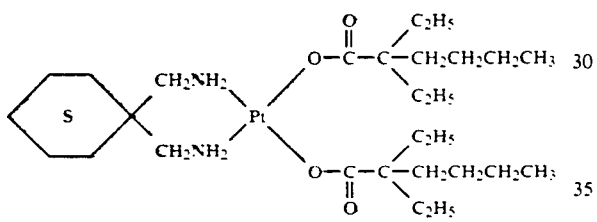

Elemental analysis of cis-bis-2,2-diethylhexanoato (trans-S,S-1,2-DACH) platinum (II) showed respective percentages for C; H; and N of 47.76%; 7.87%; and 4.22%; as compared to the calculated percentages of 47.92%; 7.99%; and 4.30%.

EXAMPLE 29

CIS-BIS-2,2-DIETHYL-4-METHYLPENTANOATO (TRANS-S,S-1,2-DACH) PLATINUM (II)

Complex #25, cis-bis-2,2-diethyl-4-methylpentanoato (trans-S,S-1,2-DACH) platinum (II) was synthesized according to synthetic route #1 using 2,2-diethyl-4-methylpentanoic acid and trans-S,S-1,2-diaminocyclohexane (DACH). The general structure of cis-bis-2,2-diethyl-4-methylpentanoato (trans-S,S-1,2-DACH) platinum (II) is as follows:

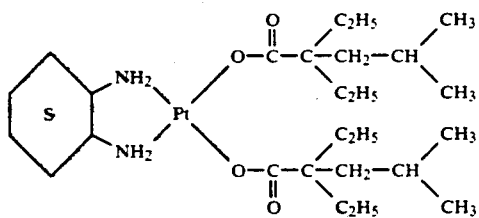

Elemental analysis of cis-bis-2,2-diethyl-4-methylpentanoato (trans-S,S-1,2-DACH) platinum (II) showed respective percentages for C; H; and N of 47.10%; 8.15%; and 4.15%; as compared to the calculated percentages of 47.92%; 7.99%; and 4.30%.

EXAMPLE 30

CIS-BIS-2,2,4,4-TETRAMETHYLPENTANOATO (TRANS-R,R-1,2-DACH) PLATINUM (II)

Complex #26, cis-bis-2,2,4,4-tetramethylpentanoato (trans-R,R-1,2-DACH) platinum (II) was synthesized according to synthetic route #1 using 2,2-4,4-tetramethylpentanoic acid and trans-R,R-1,2-diaminocyclohexane (DACH). The general structure of cis-bis-2,2,4,4-tetramethylpentanoato (trans-R,R-1,2-DACH) platinum (II) is as follows:

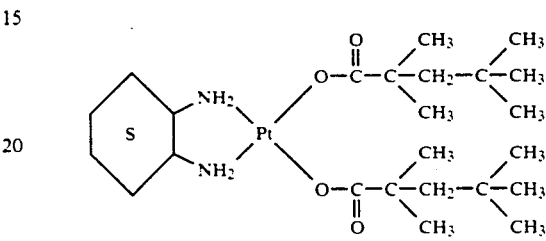

Elemental analysis of cis-bis-2,2,4,4-tetramethylpentanoato (trans-R,R-1,2-DACH) platinum (II) showed respective percentages for C; H; and N of 45.93%; 7.83%; and 4.47%; as compared to the calculated percentages of 46.22%; 7.70%; and 4.49%.

EXAMPLE 31

CIS-BIS-NEODECANOATO (cis-1,2-DIAMINOCYCLOHEXANE) PLATINUM (II)

Complex #27, cis-bis-neodecanoato (cis-1,2-diaminocyclohexane) platinum (II) was synthesized according to synthetic route #1 using an isomeric mixture of neodecanoic acids and cis-1,2-diaminocyclohexane (DACH). The general structure of cis-bis-Neodecanoato (cis-1,2-DACH) platinum (II) is as follows:

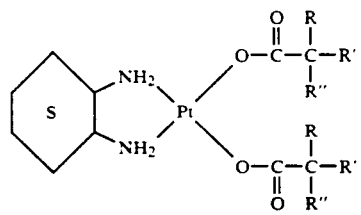

where R,R' and R" are each methyl, ethyl, propyl or isopropyl and together have eight carbon atoms. Elemental analysis of cis-bis-Neodecanoato (cis-1,2-DACH) platinum (II) showed respective percentages for C; H; and N of 46.86%; 8.13%; and 4.27%; as compared to the calculated percentages of 46.23%; 7.70%; and 4.49%.

EXAMPLE 32

THE PREPARATION OF LIPOSOMAL PREPARATIONS CONTAINING HYDROPHOBIC PLATINUM COMPLEXES

Multilamellar lipid vesicles (MLV) or liposomes containing incorporated platinum complexes of the above descriptions were prepared as previously described for other compounds (Lopez-Berestein et al. (4)(1984) Clin. Exp. Metastasis V 2 pp 127–137 and Lopez-Berestein et al. (1983) J. Inf. Dis. V 147 pp 937–945). In brief, chloroform solutions of lipids (at the desired molar ratio) and platinum complex were mixed at a lipid-PT ratio of 15:1 and the chloroform was evaporated in a rotary evaporator (Buchi, Brinkmann Instruments, Westbury, N.Y.). The dried lipid film obtained, containing platinum complex, was then dispersed with an aqueous solution (0.9% NaCl in water) by vigorous handshaking. The suspension was subsequently centrifuged at 30,000×g for 45 minutes, the supernatant was discarded, and the pellet containing platinum complex was resuspended in 0.9% NaCl solution.

MLV or liposomes containing platinum complexes may also be prepared from a lyophilized powder containing lipid and platinum compound. The lipid and platinum compound are dissolved in the hydrophobic solvent tertiary butanol (M.P. 26° C.) at the ratios described above. The solution is freeze-dried and a white powder obtained. MLV containing the platinum compound are formed upon the addition of 0.9% NaCl solution in water to the lyophilized powder with mild shaking by hand.

An alternative method for the preparation of liposomes containing different platinum complexes has been developed as follows:

1. The drug and the lipids in chloroform are mixed at an adequate drug: lipid weight ratio.
2. The chloroform is evaporated in a rotary evaporator.
3. The dry lipid film is dissolved in t-butanol.
4. The solution of drug and lipids in t-butanol is lyophilized overnight. A white, flaky powder is obtained.
5. Multilamellar liposomes containing platinum complexes are formed by adding an aqueous solution to the dry powder and mild handshaking for 1–20 minutes, depending on the drug being used. Entrapment and size distribution are similar to those obtained with other methods of liposome preparation described herein.

EXAMPLE 33

IN VIVO ANTITUMOR ACTIVITY OF LIPOSOMALLY ENCAPSULATED PLATINUM COMPLEXES AGAINST L1210 MOUSE LEUKEMIA

The in vivo antitumor activity of liposomal encapsulated platinum complexes in liposomes of DMPC:DMPG 7:3 was tested in an L1210-BDF$_1$ mouse model. BDF$_1$ mice were purchased from Charles River (Wilmington, Mass.). Groups of 6–8 mice weighing 18–22 gm were inoculated ip with 1×10$^6$ L1210 leukemia cells on day 0. L1210 cells were kept in DBA$_2$ mice with weekly passages between the different experiments. All liposomal encapsulated platinum complexes preparations were injected ip in volumes of 0.1 to 0.3 ml 24 hours after tumor inoculation. The doses of liposomal complexes used were ones that had resulted in a maximum antitumor activity in previous experiments. The doses of liposomal platinum complexes used ranged from 25 mg/kg to 50 mg/kg (approximate Clinical behavior and survival times were monitored until all animals had died. Results were expressed as % T/C (median survival time of treated mice/median survival time of control mice ×100). All preparations tested for antitumor activity were prepared under sterile conditions on the same day of the experiment. The effect of a single ip dose of various PT(II) complexes in liposomes (DMPC:DMPG 7:3) in the treatment of L1210 leukemia was tested. The T/C for cis platinum at a dose of 10 mg was 175.

The following table shows the optimal dose and T/C data for certain compounds of the present invention.

TABLE 2

OPTIMAL DOSE AND ANTITUMOR ACTIVITY AGAINST IP L1210 LEUKEMIA

| Liposomal preparation | Optimal Dose mg/kg | % T/C |
|---|---|---|
| 1 | 50 | 162 |
| 2 | 50 | 375 |
| 3 | 50 | 165 |
| 4 | 50 | 162 |
| 5 | 100 | 162 |
| 6 | 50 | 172 |
| 7 | 50 | 200 |
| 8 | 25 | 175 |
| 9 | 25 | 225 |
| 10 | 25 | 228 |
| 11 | 50 | >150 |
| 12 | 50 | 120 |
| 13 | 50 | >150 |
| 14 | 25 | >150 |
| 15 | 50 | >150 |
| 16 | 25 | 162 |
| 17 | 50 | 162 |
| 18 | 25 | 316 |
| 19 | 25 | 357 |
| 20 | 50 | 212 |
| 21 | 25 | 225 |
| 22 | 25 | 150 |
| 23 | 50 | 210 |
| 24 | 50 | 190 |
| 25 | 50 | 160 |
| 26 | 50 | 150 |
| 27 | 25 | 170 |

EXAMPLE 34

CALCULATION OF ENCAPSULATION EFFICIENCY (EE)

Elemental platinum (Pt) was determined in the liposome suspension and the pellet by x-ray fluorescence as previously reported (Seifert et al. (1979) Proc. Amer. Ass'n. Cancer Res. V 20 p. 168) in the Department of Analytical Chemistry, the University of Texas medical School at Houston, Tex. The amount of platinum complex (PT) was determined in the supernatant by ultraviolet (UV) spectrophotometry using a wavelength of 224 nm. The EE was initially calculated with the two following formulas:

1. EE = Pt in pellet/total Pt in the initial liposome suspension
2. EE = Total Pt initially added - Pt in supernatant/total Pt initially added Since the results obtained by these two methods were highly comparable and the second method only requires Pt determination by UV spectrophotometry, most EE determinations were calculated with the second method.

The following Table shows encapsulation efficiencies for complexes of the present invention.

TABLE 2

ENCAPSULATION EFFICIENCY

| Liposomal preparation # | Encapsulation % |
|---|---|
| 1 | 90 |

TABLE 2-continued

ENCAPSULATION EFFICIENCY

| Liposomal preparation # | Encapsulation % |
|---|---|
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 80 |
| 14 | 94 |
| 15 | 94 |
| 16 | 100 |
| 17 | 100 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 100 |

What is claimed is:

1. A platinum (II) four-coordinate complex having the formula:

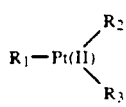

wherein $R_1$ is an alkyl diamine or cycloalkyl diamine and $R_2$ and $R_3$ are each a hydrophobic alkylcarboxylato containing from five to fourteen carbon atoms.

2. The platinum (II) four-coordinate complex of claim 1 wherein $R_1$ is trans-D,L-1,2-diaminocyclohexane, trans-R,R-1,2-diaminocyclohexane, trans-S,S-1,2-diaminocyclohexane, cis-1,2-diaminocyclohexane, ethylene diamine or 1,1-bis(aminomethyl)cyclohexane.

3. The platinum (II) four-coordinate complex of claim 1 wherein $R_2$ and $R_3$ are neohexanoato, neoheptanoato, neononanoato, neodecanoato, neooctanoato, neopentanoateo, 2-ethylhexanoato, 2-ethylbutyrato, 2-propylpropanoato, 2-methyl-2-ethylheptanoato, 2,2-diethylhexanoato, 2,2-dimethyl-4-ethylhexanoato, 2,2-diethyl-4-methylpentanoato, 2,2-dimethyloctanoato, 2-methyl-2-ethylheptanoato, 2,2-diethylhexanoato, 2,2-diethyl-4-methylpentanoato or 2,2,4,4-tetramethylpentanoato.

4. A platinum (II) four-coordinate complex, cis-bis-neohexanoato (trans-R,R-1,2-DACH) platinum (II) $H_2O$.

5. A platinum (II) four-coordinate complex, cis-bis-neoheptanoato (trans-R,R-S,S-1,2-DACH) platinum (II).

6. A platinum (II) four-coordinate complex, cis-bis-neononanoato (trans-R,R-S,S-1,2-DACH) platinum (II).

7. A platinum (II) four-coordinate complex, cis-bis-neohexanoato [1,1-bis (aminomethyl)cyclohexane] platinum (II)

8. A platinum (II) four-coordinate complex, cis-bis-neodecanoato [1,1-bis (aminomethyl)cyclohexane] platinum (II).

9. A platinum (II) four-coordinate complex, cis-bis-neoheptanoato (trans-R,R-1,2-DACH) platinum (II).

10. A platinum (II) four-coordinate complex, cis-bis-neoheptanoato [1,1-bis (aminomethyl)cyclohexane] platinum (II).

11. A platinum (II) four-coordinate complex, cis-bis-2,2-dimethyloctanoato (trans-R,R-1,2-DACH) platinum (II).

12. A platinum (II) four-coordinate complex, cis-bis-neononanoato (trans-R,R-1,2-DACH) platinum (II).

13. A platinum (II) four-coordinate complex, cis-bis-neoheptanoato (ethylenediamine) platinum (II).

14. A platinum (II) four-coordinate complex, cis-bis-neopentanoato [1,1-bis (aminomethyl)cyclohexane] platinum (II).

15. A platinum (II) four-coordinate complex, cis-bis-neononanoato [1,1-bis (aminomethyl)cyclohexane] platinum (II).

16. A platinum (II) four-coordinate complex, cis-bis-2-ethylhexanoato (trans-R,R-S,S-1,2-DACH) platinum (II) $H_2O$.

17. A platinum (II) four-coordinate complex, cis-bis-ethylbutyrato (trans-R,R-S,S-1,2-DACH) platinum (II) $H_2O$.

18. A platinum (II) four-coordinate complex, cis-bis-propylpentanoato (trans-R,R-S,S-1,2-DACH) platinum (II) $H_2O$.

19. A platinum (II) four-coordinate complex, cis-bis-2-methyl-2-ethylheptanoato (trans-R,R-1,2-DACH) platinum (II).

20. A platinum (II) four-coordinate complex, cis-bis-2,2-diethylhexanoato (trans-R,R-1,2-DACH) platinum (II).

21. A platinum (II) four-coordinate complex, cis-bis-2,2-dimethyl-4-ethylhexanoato (trans-R,R-1,2-DACH) platinum (II).

22. A platinum (II) four-coordinate complex, cis-bis-2,2-diethyl-4-methylpentanoato (trans-R,R-1,2-DACH) platinum (II).

23. A platinum (II) four-coordinate complex, cis-bis-2,2-dimethyloctanoato (trans-S,S-1,2-DACH) platinum (II).

24. A platinum (II) four-coordinate complex, cis-bis-2-methyl-2-ethylheptanoato (trans-S,S-1,2-DACH) platinum (II).

25. A platinum (II) four-coordinate complex, cis-bis-2,2-diethylhexanoato (trans-S,S-1,2-DACH) platinum (II).

26. A platinum (II) four-coordinate complex, cis-bis-2,2-diethyl-4-methylpentanoato (trans-S,S-1,2-DACH) platinum (II).

27. A platinum (II) four-coordinate complex, cis-bis-2,2,4,4-tetramethylpentanoato (trans-R,R-1,2-DACH) platinum (II).

28. A platinum (II) four-coordinate complex, cis-bis-neodecanoato (cis-1,2-diaminocyclohexane platinum (II).

* * * * *

UNITED STATES PATENT AND TRADEMARK OFFICE
CERTIFICATE OF CORRECTION

PATENT NO. : 5,117,022
DATED : May 26, 1992
INVENTOR(S) : Khokhar et al

Page 1 of 3

It is certified that error appears in the above-indentified patent and that said Letters Patent is hereby corrected as shown below:

On the title page, Item [63], under the heading "Related U.S. Application Data", "Serial No. 788,850" should read —Ser. No. 788,750—.

At column 1, line 28, "sdevelopment" should be —development—.

At column 3, line 57, "lipoosomal" should be —liposomal—.

At column 6, line 61, "platinum (II).H$_2$O" should be —platinum (II)·H$_2$O—.

At column 7, line 19, "platinum (II).H$_2$O" should be —platinum (II)·H$_2$O—.

At column 7, line 21, "platinum (II).H$_2$O" should be —platinum (II)·H$_2$O—.

At column 7, line 22, "platinum (II).H$_2$O" should be —platinum (II)·H$_2$O—.

At column 10, line 6, "PLATINUM (II).H$_2$O" should be —PLATINUM (II)·H$_2$O—.

At column 12, line 64, "CHCl" should be —CHCl$_3$—.

At column 13, line 54, "Ba(OH)$_2$.8 H$_2$O" should be —Ba(OH)$_2$·8 H$_2$O—.

At column 16, line 60, "PLATINUM (II).H$_2$O" should be —PLATINUM (II)·H$_2$O—.

UNITED STATES PATENT AND TRADEMARK OFFICE
CERTIFICATE OF CORRECTION

PATENT NO. : 5,117,022
DATED : May 26, 1992
INVENTOR(S) : Khokhar et al

It is certified that error appears in the above-indentified patent and that said Letters Patent is hereby corrected as shown below:

At column 16, line 64, "platinum (II) H₂O" should be --platinum (II)·H₂O--.

At column 17, line 20, "PLATINUM (II).H₂O" should be --PLATINUM (II)·H₂O--.

At column 17, line 22, "platinum (II) H₂O" should be --platinum (II)·H₂O--.

At column 17, line 46, "PLATINUM (II).H₂O" should be --PLATINUM (II)·H₂O--.

At column 17, line 49, "platinum (II).H O" should be --platinum (II)·H₂O--.

At column 20, line 42, "(II), cis-bis-2,2-dimethyl-4-ethylhexanoato" should be --(II), cis-bis-2,2-dimethyl-4-ethylhexanoato--.

At column 23, line 63, after "(approximate" should be inserted --LD₁₀).--

UNITED STATES PATENT AND TRADEMARK OFFICE
CERTIFICATE OF CORRECTION

PATENT NO. : 5,117,022
DATED : May 26, 1992
INVENTOR(S) : Khokhar et al

It is certified that error appears in the above-indentified patent and that said Letters Patent is hereby corrected as shown below:

At column 24, line 45, "medical" should be --Medical--.

Signed and Sealed this

Twelfth Day of October, 1993

Attest:

BRUCE LEHMAN

*Attesting Officer*    *Commissioner of Patents and Trademarks*